United States Patent [19]
McConnaughey et al.

[11] Patent Number: 4,478,792
[45] Date of Patent: Oct. 23, 1984

[54] COLORIMETRIC GAS DOSIMETER

[75] Inventors: Paul W. McConnaughey; Elmer S. McKee, both of Pittsburgh, Pa.

[73] Assignee: Mine Safety Appliances Company, Pittsburgh, Pa.

[21] Appl. No.: 532,682

[22] Filed: Sep. 16, 1983

[51] Int. Cl.$^3$ .................... G01N 21/78; G01N 31/22
[52] U.S. Cl. ........................ 422/56; 422/58; 422/60; 422/86; 436/902
[58] Field of Search .................. 422/56–60, 422/86–88; 436/164, 167, 169, 170, 902; 435/805

[56] References Cited

U.S. PATENT DOCUMENTS

| | | | |
|---|---|---|---|
| 3,723,064 | 3/1973 | Liotta | 422/56 X |
| 3,847,552 | 11/1974 | Hobgood et al. | 422/56 X |
| 4,076,502 | 2/1978 | Dugle et al. | 422/58 X |
| 4,256,694 | 3/1981 | McAllister et al. | 422/86 X |
| 4,271,121 | 6/1981 | Diller et al. | 436/902 X |

FOREIGN PATENT DOCUMENTS 2416047 10/1975 Fed. Rep. of Germany ........ 422/56

Primary Examiner—Michael Marcus
Assistant Examiner—Michael S. Gzybowski

[57] ABSTRACT

A gas dosimeter comprises a stack of porous sheets, impregnated with a reagent that changes color on contact with the gas to be determined, contained in a housing which has an opening to expose one end of the stack to the atmosphere to be tested. The gas to be determined penetrates by diffusion the layers of porous sheets, causing the sheets in the stack to change color sequentially from the end of the stack exposed to the atmosphere. The degree of penetration through the layers of porous sheets is a function of dosage exposure. The housing may be transparent with each superposed sheet in the stack being larger than the adjacent underlying sheet, so that each sheet is visible through the housing endwall.

5 Claims, 4 Drawing Figures

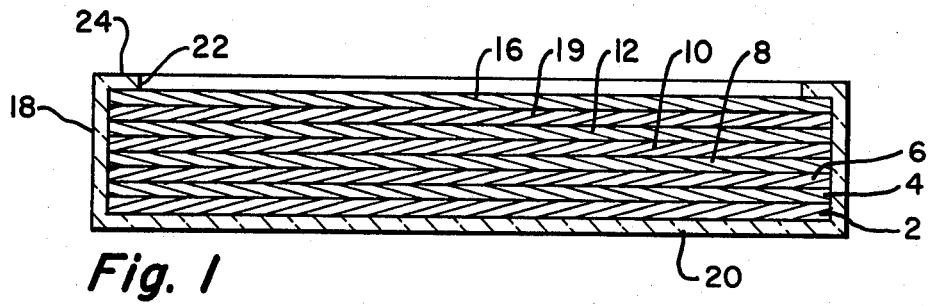
Fig. 1
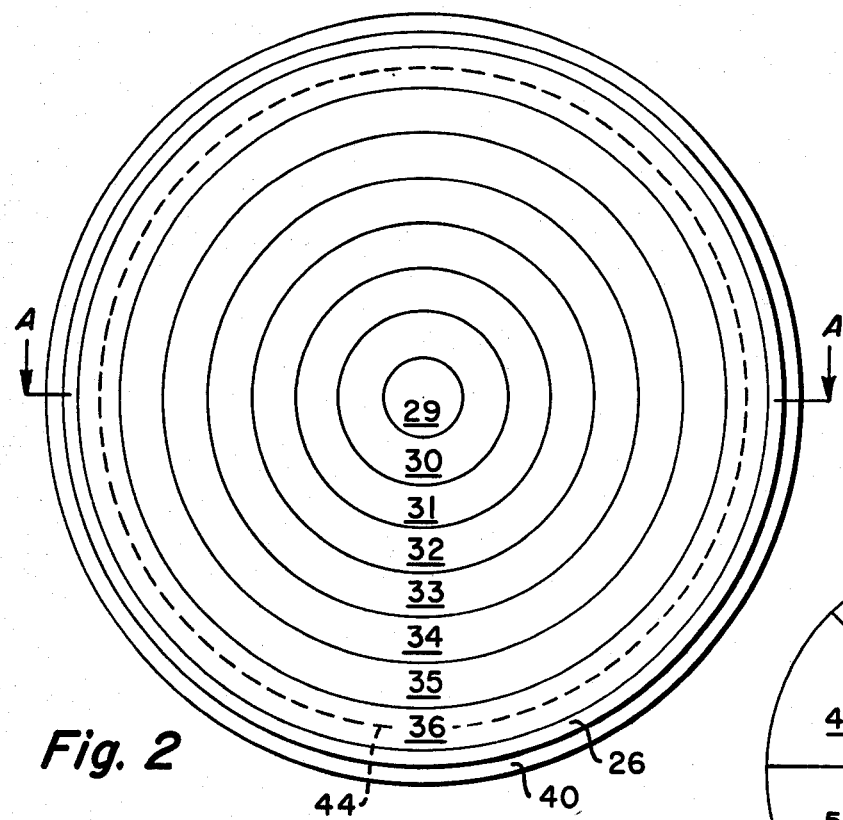
Fig. 2
Fig. 3
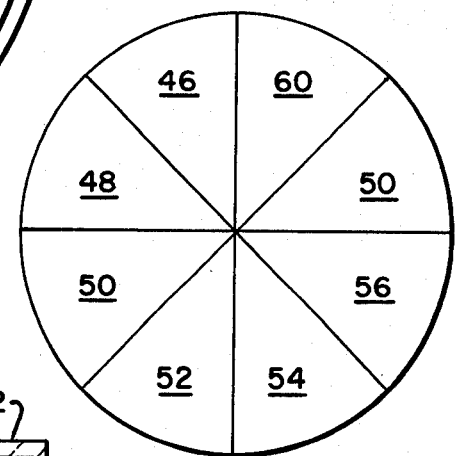
Fig. 4

4,478,792

COLORIMETRIC GAS DOSIMETER

BACKGROUND OF THE INVENTION

This invention relates to colorimetric dosimeters for determining dosage exposure to noxious gases in the atmosphere.

In colorimetric gas dosimeters a color-changing reagent is exposed to ambient air, usually through a diffusion path to minimize convection current errors, and the amount of color development is a measure of the dosage exposure to the detected gas. Dosage exposure is the integral over a time period of the concentration x time product. The "8-hour time weighted average" exposure to toxic gases, proscribed by OSHA as permissible exposure limits, is the dosage exposure over an 8-hour period divided by 8.

The color comparison type of dosimeter conventionally exposes an entire major surface of a reagent impregnated paper or similar substrate to the atmosphere. The exposure causes a spectrum of color change or variations depending on the dosage exposure. The exposed paper is compared to one or more color standards in order to read out the dosage exposure. Color comparison methods suffer inaccuracies because of wide individual subjective differences in comparing colors.

One length-of-stain type colorimetric dosimeter has an elongate bed of indicating chemical, usually with an active component on an inert granular carrier, disposed in a glass tube. Gas to be detected diffuses from an open end of the tube to and through the bed; a color change develops lengthwise of the bed, the length-of-stain being a measure of the dosage exposure. Such tubes have been widely used for measuring CO dosage. However, for many gases, and as exposure criteria are tightened, conventional length of stain tubes are not sufficiently sensitive to measure small doses. The length-of-stain developed for a given dosage is proportional to the amount of active component, but when the amount of active chemical is decreased to increase sensitivity, the intensity of the developed color also diminishes making it difficult to see the stain.

McKee and McConnaughey, U.S. Pat. No. 4,348,358, disclose a length-of-stain type dosimeter of improved sensitivity in which the reagent is carried on a strip disposed lengthwise in a transparent tube open at one end through a diffusion path to the atmosphere; dosage is determined by the length of the strip that changes color. Although this dosimeter is more sensitive than prior length-of-stain devices, even more sensitivity is desirable and needed for practical determination of dosage exposure to some noxious gases.

SUMMARY OF THE INVENTION

It is an object of this invention to provide a colorimetric gas dosimeter of increased sensitivity that is easy to read. Another object is to provide a dosimeter that will respond to instantaneous or short time exposure to noxious gases. Other objects and advantages will be apparent from the description and claims.

The gas dosimeter of the invention comprises a stack of porous sheets, impregnated with a reagent that changes color on contact with the gas to be determined, contained in a housing which has an opening to expose one end of the stack to the atmosphere to be tested. The gas to be determined penetrates by diffusion the layers of porous sheets, causing the sheets in the stack to change color sequentially from the end of the stack exposed to the atmosphere. The gas diffusion is driven by the partial pressure of the determined gas in the atmosphere, the partial pressure at the reacting front with the reagent being substantially zero. Thus the degree of penetration through the layers of porous sheets is a function of the gas concentration in the atmosphere for a given time period, i.e., dosage exposure. At the end of the testing period, the sheets can be removed and the number of color changed sheets counted. The last color changed sheet may show the change only on one side if the gas to be determined has not entirely penetrated the sheet.

In a preferred embodiment, a transparent housing endwall is shaped to conform to and receive the stack of porous sheets, each superposed sheet in the stack being larger than the adjacent underlying sheet that is closer to the endwall. Each sheet is visible through the endwall so dosage exposure is readily determined by observing the number of sheets that have changed color.

BRIEF DESCRIPTION OF THE DRAWINGS

FIG. 1 is a cross sectional view of a dosimeter according to the invention.

FIG. 2 is a bottom view of a dosimeter having a transparent housing.

FIG. 3 is a cross section taken on line A—A of FIG. 2.

FIG. 4 is a diagrammatic representation of another configuration of a dosimeter having a transparent housing.

DESCRIPTION OF THE PREFERRED EMBODIMENTS

Referring to FIG. 1, the dosimeter comprises a stack of porous sheets 2, 4, 6, 8, 10, 12, 14 and 16 contained in a cylindrical housing 18 with an endwall 20 and an opening 22 opposite the endwall. The opening is defined by inwardly extending flange 24 that engages the top sheet 16 of the stack.

The porous sheets are impregnated with a reagent that changes color when contacted with the gas to be determined and act as diffusion barriers through which the gas diffuses. Any porous sheet material may be used that is substantially inert to the reagent and the atmosphere to be tested, such as, for example, cloth, felt, paper or microporous synthetic polymer membranes. Filter papers are preferred as they are readily available in uniform quality and a variety of materials.

The top sheet 16 may be unimpregnated and used as a windshield so that the impregnated layers are responsive only to gas transported by diffusion. If the top sheet 16 is impregnated with reagent, wind or air currents may increase the rate of color change in sheet 16; although this may result in some minor inaccuracies in dosage exposure measurement, it may be desirable to provide a rapid indication of exposure.

In the embodiment of FIG. 2 and FIG. 3, the dosimeter body 26 is molded from a transparent material, suitably plastic or glass, and has a stepped cavity 28 that conforms to and receives the stack of porous discs 29, 30, 31, 32, 33, 34, 35 and 36. Each of the overlying discs is larger in diameter than the adjacent underlying disc, the largest disc 36 being most remote from the endwall 38, so that each disc is visible through the transparent endwall. The discs are impregnated with colorimetric reagent, except that disc 36 may be unimpregnated if it is desired to use it as a windscreen. The cover 40 tightly engages the outside surface of body sidewall and has an inwardly extending flange 42 that defines opening 44 and engages disc 36. This dosimeter operates in the same manner as the dosimeter of FIG. 1 and has the additional advantage that the number of discs that have changed color can be observed without removing them from the housing.

FIG. 4 is a diagrammatic view of an alternative configuration of a dosimeter having a transparent body. The stack of reagent-impregnated porous sheets are successively larger segments of a circle. The sheet 46 most remote from the dosimeter opening is ⅛ of the circle; the next adjacent sheet 48 is ¼ of a circle, one edge of which is aligned with an edge of segment 46 so that a ⅛ segment of sheet 48 is visible through the dosimeter endwall; the next segment 50, a ⅜ segment of the circle, is similarly aligned so that a ⅛ segment is visible; ½ segment 52, ⅝ segment 54, ¾ segment 56, and ⅞ segment 58 are similarly aligned and partially visible; full disc 60 completes the stack and is exposed to the atmosphere to be tested. The degree of exposure is readily observable by observing the proportion of the circle, visible through the dosimeter body, that has changed color.

It will be recognized that the dosimeters of this invention are generally useable with any colorimetric reagent used for determining gases. The sensitivity and range of measurable dosage exposure can be varied by adjusting the porous sheet material, its thickness, or the amount or composition of impregnated reagent.

EXAMPLE 1

Whatman No. 1 filter paper was impregnated with a solution of 0.020 g. of bromophenol blue (sodium salt) in 180 cc. of water and 20 cc. of glycerine and air dried. Eight layers of indicating papers, 37 mm. in diameter, were stacked in housing having a 33 mm. opening exposing one end of the stack to an atmosphere containing 10 ppm. of chlorine in air. The layers of paper that changed color (blue to white) were:

| Time Exposed (Minutes) | Layers of Paper that Changed Color | Dosage Exposure (ppm - hrs) |
|---|---|---|
| 0 | 0 | 0 |
| 15 | 2 | 2½ |
| 35 | 3 | 5 5/6 |
| 60 | 4½* | 10 |
| 95 | 6¼ | 15 5/6 |
| 120 | 7 | 20 |

*½ indicates one side only changed color.

EXAMPLE 2

Eight layers of lead acetate paper 37 mm. discs (Whatman #1 paper wet with 0.32% lead acetate in 95/% water—5% glycerin and air dried) were stacked in a dosimeter housing having a one-inch diameter opening, and exposed to air containing 10 ppm. hydrogen sulfide with the following results:

| Time Exposed (Minutes) | Layers of Paper that Changed Color | Dosage Exposure (ppm - hrs) |
|---|---|---|
| 0 | 0 | |
| 15 | 1 | 2½ |
| 32 | 2¼ | 5¼ |
| 60 | 3 | 10 |
| 90 | 4½ | 15 |
| 120 | 5 | 20 |
| 180 | 7 | 30 |

EXAMPLE 3

A dosimeter like that of Example 2, except that an unimpregnated disc of Whatman #1 paper was used as a windshield, was exposed to air containing 20 ppm. hydrogen sulfide with the following results:

| Time Exposed (Minutes) | Layers of Paper that Changed Color | Dosage Exposure (ppm - hrs) |
|---|---|---|
| 0 | 0 | 0 |
| 15 | 1 | 5 |
| 45 | 2.5 | 15 |
| 105 | 5 | 35 |
| 165 | 8 | 55 |

I claim:

1. A gas dosimeter comprising a stack of superposed porous sheets contained in a housing; the housing having a sidewall, a transparent endwall and means defining an opening opposite the endwall; each superposed sheet is of a larger cross-sectional area than the adjacent underlying sheet, the largest sheet being most remote from the transparent endwall and extending across the cross-sectional area of the opening; and at least each of the porous sheets, except the most remote sheet being impregnated with a reagent that changes color on contact with the gas to be determined.

2. A dosimeter of claim 1 in which the sheets are filter paper.

3. A dosimeter of claim 1 in which the sheets are discs.

4. A dosimeter of claim 1 in which the sheets are segments of a circle.

5. A dosimeter of claim 1 in which the housing comprises a cup-shaped body comprising the endwall and sidewall, and said opening means comprises a cover tightly engaging an outer surface of the sidewall and having an inwardly extending flange defining the opening and engaging the stack.

* * * * *